(12) United States Patent
Graham et al.

(10) Patent No.: US 10,328,190 B2
(45) Date of Patent: Jun. 25, 2019

(54) IMPLANTATION OF A TRANSAPICAL VENTRICULAR ASSIST DEVICE AND KIT FOR SAME

(71) Applicant: HeartWare, Inc., Miami Lakes, FL (US)

(72) Inventors: Joel Graham, Louisville, KY (US); Charles R. Shambaugh, Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 247 days.

(21) Appl. No.: 15/497,670

(22) Filed: Apr. 26, 2017

(65) Prior Publication Data

US 2017/0224896 A1    Aug. 10, 2017

Related U.S. Application Data

(62) Division of application No. 14/799,703, filed on Jul. 15, 2015, now Pat. No. 9,656,011.

(60) Provisional application No. 62/025,119, filed on Jul. 16, 2014.

(51) Int. Cl.
*A61M 1/12* (2006.01)
*A61M 1/10* (2006.01)

(52) U.S. Cl.
CPC .......... *A61M 1/122* (2014.02); *A61M 1/1008* (2014.02); *A61M 1/1036* (2014.02); *A61M 1/101* (2013.01); *A61M 1/125* (2014.02); *A61M 2205/04* (2013.01); *A61M 2205/3331* (2013.01); *A61M 2205/3337* (2013.01); *A61M 2210/125* (2013.01)

(58) Field of Classification Search
CPC .. A61M 1/1018; A61M 1/1008; A61M 1/122; A61M 1/125
See application file for complete search history.

(56) References Cited

U.S. PATENT DOCUMENTS

| | | |
|---|---|---|
| 3,814,547 A | 6/1974 | Kitrilakis et al. |
| 4,994,078 A | 2/1991 | Jarvik |
| 2004/0059178 A1 | 3/2004 | McCarthy et al. |
| 2007/0167968 A1 | 7/2007 | Pandey |
| 2011/0124950 A1 | 5/2011 | Foster |

(Continued)

FOREIGN PATENT DOCUMENTS

| | | |
|---|---|---|
| CN | 101678158 A | 3/2010 |
| CN | 102553005 A | 7/2012 |

OTHER PUBLICATIONS

Notice on the First Office Action, Search Report and Text of the First Office Action, dated Aug. 28, 2018 for corresponding Application No. 201580048874.7, filed Jul. 15, 2015, 6 pages.

(Continued)

*Primary Examiner* — Michael W Kahelin
(74) *Attorney, Agent, or Firm* — Christopher & Weisberg, P.A.

(57) ABSTRACT

A method of implanting a blood pump in a heart of a mammalian subject includes maintaining a temporary plug in an inlet opening of a pump having a pump body and an outlet cannula projecting from the pump body, advancing the pump into a ventricle of the heart through a hole in a wall of the heart so that the inlet of the pump is disposed within the ventricle and the outlet cannula extends through a valve of the heart into an artery, and then withdrawing the temporary plug from the inlet of the pump.

11 Claims, 6 Drawing Sheets

(56) References Cited

U.S. PATENT DOCUMENTS

2013/0042892 A1   2/2013  Lynch
2015/0038770 A1   2/2015  Colella
2015/0112120 A1   4/2015  Andrus

OTHER PUBLICATIONS

International Search Report and Written Opinion dated Oct. 23, 2015, for corresponding International Application No: PCT/US2015/040577; International Filing Date: Jul. 15, 2015 consisting of 8 pages.

IMPLANTATION OF A TRANSAPICAL VENTRICULAR ASSIST DEVICE AND KIT FOR SAME

CROSS-REFERENCE TO RELATED APPLICATION

This application is a divisional of U.S. patent application Ser. No. 14/799,703 (now U.S. Pat. No. 9,656,011), filed Jul. 15, 2015, entitled IMPLANTATION OF A TRANSAPICAL VENTRICULAR ASSIST DEVICE AND KIT FOR SAME, and claims priority to U.S. Provisional Application Ser. No. 62/025,119, filed Jul. 16, 2014, the entirety of which is incorporated herein by reference.

TECHNICAL FIELD

The present invention relates to a blood pump, and, more particularly, relates to a system and method for facilitating implantation of a blood pump.

BACKGROUND

In certain disease states, the heart lacks sufficient pumping capacity to meet the needs of the body. This inadequacy can be alleviated by providing a mechanical pumping device referred to as a ventricular assist device ("VAD") to supplement the pumping action of the heart. Considerable effort has been devoted to providing a VAD which can be implanted and which can remain in operation for months or years to keep the patient alive while the heart heals (bridge-to-recovery), or which can remain in operation permanently (destination therapy) or until a suitable donor heart becomes available if the heart does not heal (bridge-to-transplantation).

The VAD is typically connected to the heart, most commonly to the left ventricle, which is responsible for pumping oxygenated blood through the aortic valve to the general body. For example, a VAD may include a pump which is installed in the body outside of the heart. The VAD may have an inlet cannula connected to the interior of the left ventricle and connected to the intake of the pump. The VAD may also include an outlet tube connected to the outlet of the pump, routed along the outside of the heart, and grafted to the aorta. Installation of a VAD, particularly a VAD that makes use of an outflow graft, often requires cardioplegia and/or a cardiopulmonary bypass ("CPB"). Cardioplegia and CPB can extend the time of the implantation procedure and has risks which can be significant.

As disclosed in commonly owned U.S. Publication No. 2009/0203957, the disclosure of which is hereby incorporated by reference herein, one solution developed to avoid the need for an outflow graft is a pump that is implantable within the left ventricle, which can pump blood disposed within the left ventricle directly through the aortic valve via an outflow cannula coupled to an outlet of the pump. Installation of such a device is typically performed by inserting the outflow cannula and pump through a cored opening in the apex of the heart. This device avoids the need for connecting an outflow cannula external to the heart, and greatly simplifies the installation procedure.

Despite the considerable efforts devoted to improvements in VADs, still further improvement would be desirable.

SUMMARY

Described herein are systems/kits, methods, and devices that facilitate implantation of a VAD within one or more chambers of the heart. In particular, one aspect of the present disclosure describes a transapical VAD that includes an axial flow pump and a pedestal. Also described is a catheter utilized in conjunction with the implantation of the VAD. The catheter desirably includes at least two lumens one of which operates a balloon and the other of which communicates with a distal end of the catheter and is capable of removing air or other fluid disposed beyond or distal to the balloon. The catheter can also include a transducer, such as a pressure transducer, capable of measuring pressure of a fluid beyond or distal to the balloon.

Also described are methods of implantation, which generally include gaining access to the apex of the heart, attaching a mounting ring to the apex, coring the apex through the mounting ring, partially inserting the VAD into the heart through the cored opening, de-airing the VAD via a catheter, continuing advancement of the VAD into the heart, measuring a physical condition within the heart, such as pressure, affixing the VAD to the heart, removing the catheter, and plugging the VAD.

Thus, in one aspect of the present disclosure, a method of implanting a blood pump in a heart of a mammalian subject includes maintaining a temporary plug in an inlet opening of a pump having a pump body and an outlet cannula projecting from the pump body. The method desirably also includes advancing the pump into a ventricle of the heart through a hole in a wall of the heart so that the inlet of the pump is disposed within the ventricle and the outlet cannula extends through a valve of the heart into an artery, and withdrawing the temporary plug from the inlet of the pump.

Additionally, the method may include mounting a ring to the wall of the heart and forming the hole in the wall of the heart within the ring. Also, the step of advancing the pump may include advancing a pedestal mechanically connected to the pump into the hole and into the ring, and securing the pedestal to the ring. The temporary plug may be mounted on an elongated catheter and the catheter may extend through a channel in the pedestal when the pump is advanced into the ventricle. Further, the step of withdrawing the temporary plug may include withdrawing the catheter and the plug through the channel in the pedestal and then closing the channel.

Continuing with this aspect, the step of maintaining the temporary plug may include maintaining the temporary plug in an expanded condition, and the step of removing the plug may include collapsing the plug. The plug may include a balloon. Also, the step of maintaining the temporary plug in an expanded condition may include maintaining the balloon in an inflated condition, and the step of collapsing the temporary plug may include deflating the balloon.

The method may also include purging the pump and the outlet cannula of air by allowing air to escape from the pump and the outlet cannula through the catheter while the outlet cannula is at least partially positioned within the heart or artery. Further, the method may include measuring pressure in the heart or artery using a pressure measurement instrument communicating with the interior of the pump through the catheter.

The ventricle may be the left ventricle and the valve may be the aortic valve. In addition, the steps of the method may be performed without cardiopulmonary bypass or cardioplegia.

In another aspect of the present disclosure, a pump installation kit comprises a pump including a pump body having an interior and an inlet communicating with the interior, a pumping element mounted within the interior, and an outlet cannula communicating with the interior of the pump body. The pump is desirably adapted for mounting with the pump body and inlet disposed within a ventricle of a heart. The kit preferably includes a temporary plug which is adapted for releasable, sealing engagement in the inlet.

Additionally, the kit may include a securement/mounting ring adapted for mounting to the outside of the heart, and a pedestal adapted for mounting to the securement ring. The pedestal may be mechanically coupled to the pump. When the pedestal is mounted to the securement ring, the pedestal may have a channel having proximal and distal ends. The distal end of the channel may communicate with the ventricle, and the proximal end of the channel may be disposed outside of the heart.

Continuing with this aspect, the kit may include an elongated element mechanically connected to the temporary plug. The elongated element may extend through the channel when the temporary plug is engaged in the inlet. The temporary plug may be adapted to pass out of the heart through the channel after the temporary plug is disengaged from the inlet port. The temporary plug may have an expanded condition and a collapsed condition, and the temporary plug may be adapted to pass out through the channel in the collapsed condition. The elongated element may be a catheter having an inflation lumen, and the temporary plug may include a balloon communicating with the inflation lumen. Also, the elongated element may be a catheter having a fluid lumen. The fluid lumen may communicate with the interior of the pump when the temporary plug is engaged in the inlet port. A pressure measuring instrument may be connectable to the fluid lumen Furthermore, the kit may include a closure adapted to seal the channel in the pedestal. The closure may include a screw adapted to threadedly engage the channel. A resilient seal may be disposed within the channel. The resilient seal may sealingly engage the elongated element and the pedestal when the elongated element is disposed within the channel. The resilient seal may be a one-way valve adapted to prevent blood flow from the proximal end of the channel when the elongate element is removed therefrom.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein, when referring to the disclosed devices, the term "proximal" means closer to the operator or in a direction toward the operator and the term "distal" means more distant from the operator or in a direction away from the operator. Also, as used herein, the terms "about," "generally," and "substantially" are intended to mean that slight deviations from absolute are included within the scope of the term so modified.

Figure 1:
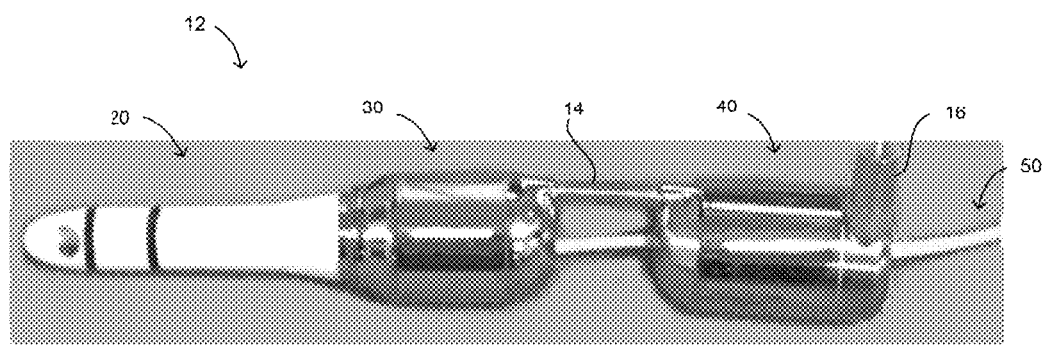
FIG. 1 is an elevational view of a transapical VAD implantation kit including a ventricular assist device and a catheter according to one embodiment of the present disclosure.

FIG. 1 depicts a transapical VAD installation kit 10 according to one embodiment of the present disclosure. Installation kit 10 generally includes a transapical VAD and a catheter 50. The transapical VAD delivers blood flow in line with the native heart and eliminates the need for CPB, cardioplegia, or an outflow graft to the aorta or pulmonary artery. The transapical VAD is generally comprised of a pump 12 and a pedestal 40 mechanically coupled to pump 12 via an elongate member 14.

Pump 12 may be generally as shown in the '957 Publication. It includes a pump body 30. Pump body 30 includes a tubular housing 37 defining an inlet port 34 at a proximal end of pump body 30 and an outlet port 35 at a distal end of pump body 30. A rotor 36 or axial flow impeller having a plurality of blades projecting outwardly therefrom is rotatably disposed within tubular housing 37. Rotor 36 may be formed from a unitary piece of magnetizable, biocompatible material, such as biocompatible platinum-cobalt or platinum-cobalt-boron alloy. Rotor 36 may be magnetically or hydrodynamically levitated within housing 37. During operation, rotor 36 is rotatable about an axis thereof by a motor stator 38 that is disposed about tubular housing 37 in order to urge fluid from inlet port 34 to outlet port 35. Motor stator 38 is configured to provide a rotating magnetic field and preferably contains magnetic laminations and wire coils. An exterior shroud 32 surrounds housing 37 and motor stator 38. Shroud 32 may be formed from any biocompatible material including, but not limited to, titanium, ceramic or polymer. Additionally, shroud 32 may be coated by a thromboresistant coating or other hemodynamically suitable coating.

Figure 2:
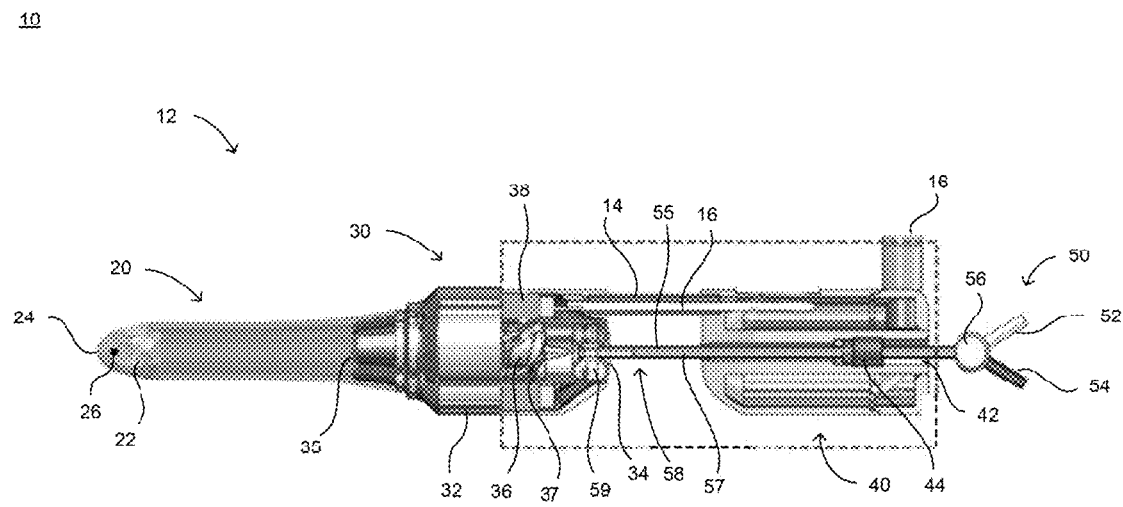
FIG. 2 is a partially sectional view depicting elements of the kit of FIG. 1.
Figure 3:
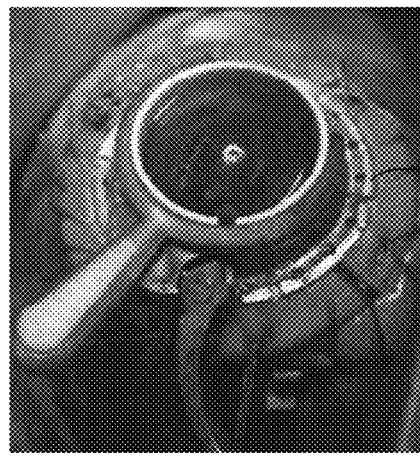
FIGS. 3-8 are perspective views depicting steps in a method of implantation using the kit of FIG. 1.
Figure 4:

Pump 12 also includes an outflow cannula 20 extending distally from outlet port 35 of pump body 30. Cannula 20 may be made from any biocompatible material including, but not limited to, metallic and/or polymeric materials, such as thermoplastic polyurethanes, silicone, polycarbonate-urethanes, polyether-urethanes, aliphatic polycarbonate, titanium, barium sulfate, and any combinations thereof. Additionally, cannula 20 may include radiopaque materials incorporated into its structure at particular locations along the length of cannula 20 to allow for radiographic determination of the cannula's positioning relative to the patient's anatomy. For example, as shown in FIG. 2, cannula 20 may include a radiopaque bead 26, such as a titanium or platinum bead, embedded within its structure at a distal end thereof, which may help with fluoroscopic visualization.

Outflow cannula 20 may be straight or bent and is generally a hollow, elongate structure that is dimensioned for partial placement into an aorta or pulmonary artery while pump body 30 is positioned in the left or right ventricles, respectively. A cross-sectional dimension of outflow cannula 20 may taper from pump body 30 such that the cross-sectional dimension near pump body 30 is larger relative to the cross-sectional dimension farther from pump body 30. For example, cannula 20 may have a larger diameter near pump body 30 and a smaller diameter at a distal end of cannula 20.

The distal end of cannula 20 is defined by a distal tip 24 that includes one or more outflow openings 22 communicating with the interior of pump body 30. Outflow cannula 20 preferably also may include internal vanes (not shown), which convert rotational momentum of blood leaving rotor 36 into useful pressure. In some embodiments, the vanes may be located proximal to distal tip 24 or may be included in pump body 30 downstream of or distal to rotor 36.

Pedestal 40 is generally a cylindrical member having a proximal to distal axis (not shown). Exemplary pedestals and methods of implantation can be found in U.S. Patent Application Publication 2015/0038770, the disclosure of which is hereby incorporated herein by reference in its entirety. Pedestal 40 includes an electrical connection 16 that is coupled to a power source and/or controller disposed outside of the heart. Electrical connection may enter into a proximal end of pedestal 40 in a transverse direction with respect to the proximal to distal axis of pedestal 40. Electrical connection 16 may be rerouted within pedestal 40 so that electrical connection 16 extends in a generally axial direction along the longitudinal axis of pedestal 40 and through elongate member 14 into pump body 30 where it is electrically coupled to motor stator 38.

A channel 42 may extend into a proximal end of pedestal 40 and exit through a distal end thereof. Channel 42 preferably has a diameter dimensioned to receive an elongate catheter therein. Additionally, pedestal 40 may be positioned respective to pump 12 such that channel 42 is coaxial with a bore of pump housing 37. A resilient seal 44 may be disposed within channel 42 to serve as a temporary seal of channel 42. For example, resilient seal 44 may be a one-way valve press-fit into channel 42. Resilient seal 44 may be configured to prohibit blood from passing proximally within channel 42. For example, resilient seal 44 may have leaflets that open in one direction. In addition, resilient seal 44 may be configured to allow catheter 50 to be passed through channel 42 in a proximal to distal direction and removed therefrom in the opposite direction, as described further below. In addition, resilient seal 44 may be configured to engage catheter 50 when disposed within channel 42 and to provide a seal around catheter 50. For example, resilient seal 42 may be made from a flexible yet resilient biocompatible material that biases toward a closed or contracted condition. In addition, channel may narrow 42 at a location distal to resilient seal 44 so as to prevent resilient seal 44 from being dislodged from pedestal 40 in a distal direction. In another embodiment, seal 44 may contract around catheter 50 to provide a temporary seal while catheter is disposed within channel 42 but may not seal channel 42 when catheter 50 is removed therefrom.

Figure 8:
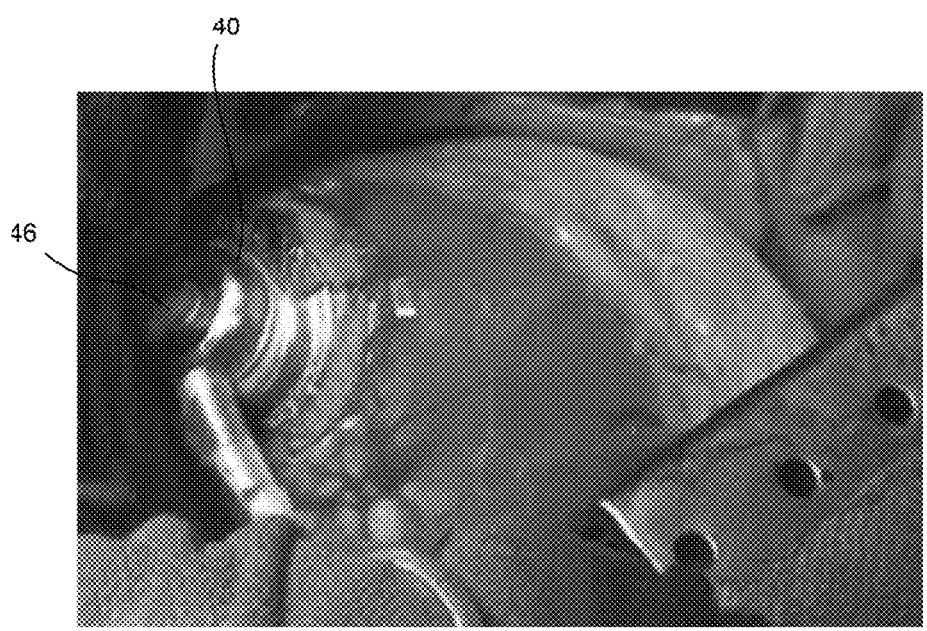

Channel 42 may be internally threaded at or near the proximal end of pedestal 40. Such threading may correspond to threading of a removable closure 46 (see FIG. 8), such as a screw. However, alternative engagement features other than threading are contemplated, such as a Morse taper, for example. As discussed below, removable closure 46 sealingly engages pedestal 40 within channel 42 after removal of the catheter to permanently seal or plug the proximal end of pedestal 40 and provide redundancy to resilient seal 44.

Pedestal 40 may serve as an intermediary between an external power supply and/or controller and pump body 30. In addition, pedestal 40 may serve as a support structure for attachment to a ventricular wall of the heart. Pedestal 40 may be made from any biocompatible material including titanium, ceramic or polymer. In addition, pedestal 40 may include a sintered coating on an outer surface thereof to promote tissue ingrowth/attachment. The outer surface may also have engagement features (not shown) for engaging sutures attached to a mounting ring to help further secure pedestal to a ventricular wall.

Catheter 50 is generally an elongate structure that includes a plurality of input/output lines 52, 54, a transition region 56 and a catheter body 58 that defines a plurality of individual lumens 55, 57 therein. Input/output lines 52, 54 converge and couple to catheter body 58 at transition region 56. Each input/output line 52, 54 communicates with a respective lumen 55, 57 within catheter body 58. Catheter body 58 may also include an expandable element 59 at a distal end thereof that has an expanded condition and a collapsed condition. As discussed below, when the expandable element 59 is in the expanded condition, it serves as a temporary plug that seals inlet port 34 of pump body 30. One example of such catheter is a Swan-Ganz® catheter (Edwards Lifesciences Corp., Irvine, Calif.).

In one embodiment, which is depicted in FIG. 2, catheter 50 may include a first input/output line or inflation line 52, which communicates with an inflation lumen 55 within catheter body 58. Additionally, catheter 50 may include a second input/output line or fluid line 54, which communicates with a fluid lumen 57 within catheter body 58. In addition, expandable element 59 is located at the distal end of catheter body 58 and takes the form of an inflatable balloon, which when inflated, surrounds a circumference of catheter body 58. Inflation lumen 55 communicates with balloon 59 such that a device, such a syringe, can be attached to inflation line 52 and deliver air or saline solution to balloon 59 via inflation lumen 55 in order to inflate balloon 59 into the expanded or inflated condition. Conversely, the air or saline solution can be withdrawn from balloon 59 and inflation lumen 55 to deflate balloon 59 into the collapsed or deflated condition. In the inflated condition, balloon 59 may seal inlet port 34 of pump 30, and in the deflated condition, catheter body 58 may be removed from pump 30 and channel 42 of pedestal 40.

Fluid lumen 57 communicates with an opening (not shown) at the distal end of catheter body 58. Such opening is preferably located beyond or distal to balloon 59. A device, such as a syringe, can be attached to fluid line 54 so that air and/or blood that is disposed beyond or distal to balloon 59 can be drawn through fluid lumen 57. For example, when balloon 59 is in an inflated condition and seals inlet port 34 of the pump, fluid lumen 57 can be used to de-air and prime pump 12.

Other lumens and corresponding individual lines for performing additional functions are also contemplated. For example, a third input/output line or sensor line (not shown) in communication with a sensor lumen within catheter body 58 may house a wire communicating with a pressure transducer disposed within fluid lumen 57 or on an exterior of catheter body 58 at a location distal to the temporary plug formed by expanded balloon 59. Such sensor line and corresponding lumen can be coupled to a processor that is capable of converting signals received from the pressure transducer into pressure measurements of a fluid disposed within fluid lumen 57. Alternatively, in one embodiment, the sensor lumen may communicate with another opening located at the distal end of catheter body 58 and sealed by a diaphragm. Deflection of the diaphragm can be measured to determine pressure of a fluid disposed at the distal end of catheter body 58. In a further embodiment, fluid line 54, or another fluid line, can be coupled to a pressure transducer, which may be located outside of the patient's body during implantation. In such embodiment, the externally situated pressure transducer can measure pressure at a distal opening of the catheter by sensing pressure of a fluid disposed within fluid lumen 57 and fluid line 54. Other known configurations used to measure physical conditions via a catheter are also contemplated.

In an alternative embodiment (not shown) of catheter 50, first line 52 and first lumen 55 may house a wire coupled to a distal tip of the catheter body 58. A sidewall of catheter body 58 at the distal end thereof may be configured to buckle and expand outwardly in the shape of disc upon the tensioning of the wire at the proximal end of catheter 50. Such configuration may be an alternative expandable element to an inflatable balloon.

FIGS. 3-7 depict an exemplary method of implanting pump 12 into a heart via kit 10. Such method generally includes gaining access to the apex of the heart, attaching a mounting ring 80 to the apex, coring the left ventricular wall through mounting ring 80, partially inserting pump 12 into the left ventricle, de-airing pump 12 via catheter 50, continuing insertion of pump 12 into the left ventricle, measuring pressure sensed by catheter 50, determining when the pressure measurements indicate that outflow cannula 20 is partially positioned within the ascending aorta, affixing pedestal 40 to the ventricular wall, deflating and removing catheter 50, and plugging pedestal 40 via the removable closure 46.

More particularly, prior to implantation of pump 12 into the left ventricle, catheter 50 is assembled with the transapical VAD by inserting catheter body 58 in a proximal to distal direction through pedestal channel 42 and resilient seal 44 such that the distal end of catheter body 58 extends into inlet port 34 of pump body 30. This may be done in the operating theater or performed in the manufacturing facility in order to pre-assemble kit 10 prior to shipment to the healthcare facility.

A syringe, or other device, is coupled to inflation lumen 52 and air or saline solution is delivered through inflation lumen 52 from the syringe to balloon 59, thereby expanding balloon 59 into its inflated condition within inlet port 42. In the inflated condition, balloon 59 serves as a temporary plug within inlet port 34. As such, rotor 36 and outflow cannula 20 are sealed from inlet port 34. Only openings 22 of outflow cannula 20 can communicate with an environment external to pump 12.

Thereafter, or concurrently with assembly of catheter 50 with the transapical VAD, an operator gains access to the heart preferably via a left subcostal or left thoracotomy incision to expose the apex of the heart. A mounting ring 80, which may be provided as part of implantation kit 10 along with a coring instrument 90, is attached to the apex via a pledgeted purse string suture, mattress suture, or the like (best shown in FIG. 3). Examples of suitable mounting rings, coring instruments, and methods of using same can be found in U.S. Patent Application Publication No. 2007/0167968, the disclosure of which is hereby incorporate by reference. Other examples of mounting rings, including mounting rings that include leafleted valves, can be found in U.S. Patent Application Publication No. 2015/0112120, the disclosure of which is hereby incorporated by reference. In addition, examples of implanting a transapical VAD through a cored opening in the left ventricle can be found in the heretofore referenced '957 publication.

A slit incision or incision in the form of a cross or X, commonly referred to as a "crux" incision, is made within mounting ring 80, through the ventricular wall and into the left ventricle. Coring instrument 90 is inserted through the crux incision and ventricular wall tissue is resected from the heart via coring instrument 90 to form a cored opening 70 (best shown in FIGS. 4 & 5). Although, it is described that mounting ring 80 is applied before coring the apex of the heart, it should be understood that other techniques in which a mounting ring is applied after cored opening 70 is formed is also applicable.

Figure 5:
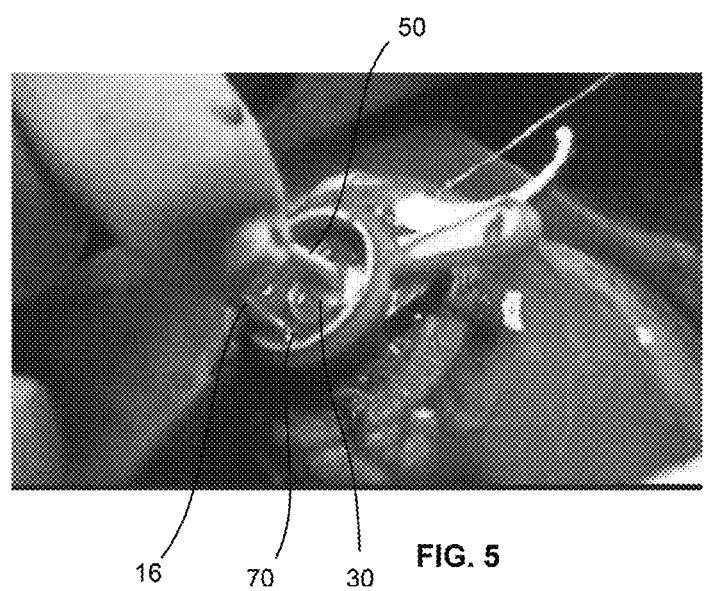

While maintaining balloon 59 in the expanded configuration, pump 12 is advanced at least partially into the cored opening 70 (best shown in FIG. 5). Such advancement can be performed quickly to help limit blood loss. Also, the operator may manually block the cored opening while maneuvering outflow cannula 20 into the opening. Blood loss can also be mitigated by a leafleted mounting ring, such as those described in the aforementioned '120 Publication and by other implantation device, examples of which can be found in U.S. Provisional Application No. 62/089,910, the disclosure of which is hereby incorporated by reference in its entirety.

Air may be trapped within pump 12 beyond or distal to inflated balloon 59. This air is removed to de-air outflow cannula 20 and pump body 30 via another device, such as a syringe, attached to fluid line 54 of catheter 50. Fluid line 54 and fluid lumen 57 communicate with a distal opening beyond or distal to inflated balloon 59. Negative pressure is applied to fluid line 54 and fluid lumen 57 via the device which in turn applies negative pressure to the pump distal to balloon 59. As such, the air located within pump 12 is drawn out of the pump and is replaced by blood. Blood entering into the device coupled to fluid line 54 indicates that pump 12 has been sufficiently de-aired. De-airing removes air that can be potentially dangerous to the patient and also primes pump 12 with blood so that pump 12 can operate effectively upon startup. Inflated balloon 59 helps prevent retrograde blood flow and blood loss during advancement of pump 12. In addition, inflated balloon 59 helps create an environment within pump 12 effective to determine blood pressure at the distal tip of outflow cannula 20.

The de-aired pump 12 is then advanced through the left ventricle. As pump 12 is advanced through the left ventricle, blood pressure may optionally be sensed by a pressure transducer located within catheter 50 and monitored by the operator. Although, the pressure transducer or sensing location of the pressure transducer may be located in the distal end of catheter body 58 proximal to rotor 36, the blood pressure detected by the sensor is substantially the same as that located at distal tip 24 of outflow cannula 20. As previously mentioned, openings 22 of outflow cannula 20 are the only openings through which the inside of pump 12 communicates with the outside environment while inlet port 34 is plugged by balloon 59. Thus, the blood pressure within outflow cannula 20 and pump body 30 is substantially the same as the blood pressure located at openings 22 of distal tip 24. There may be a small offset between pressure sensed by the pressure transducer and pressure at distal tip 24 of outflow cannula 20. However, such offset is minimal particularly in comparison to the differences between ventricular pressure and aortic pressure, which is significant. Thus, the operator can use the pressure measurements taken by the pressure transducer, particularly a measured difference between ventricular pressure and aortic pressure, to determine the location of distal tip 24 relative to the patient's anatomy.

Figure 6:
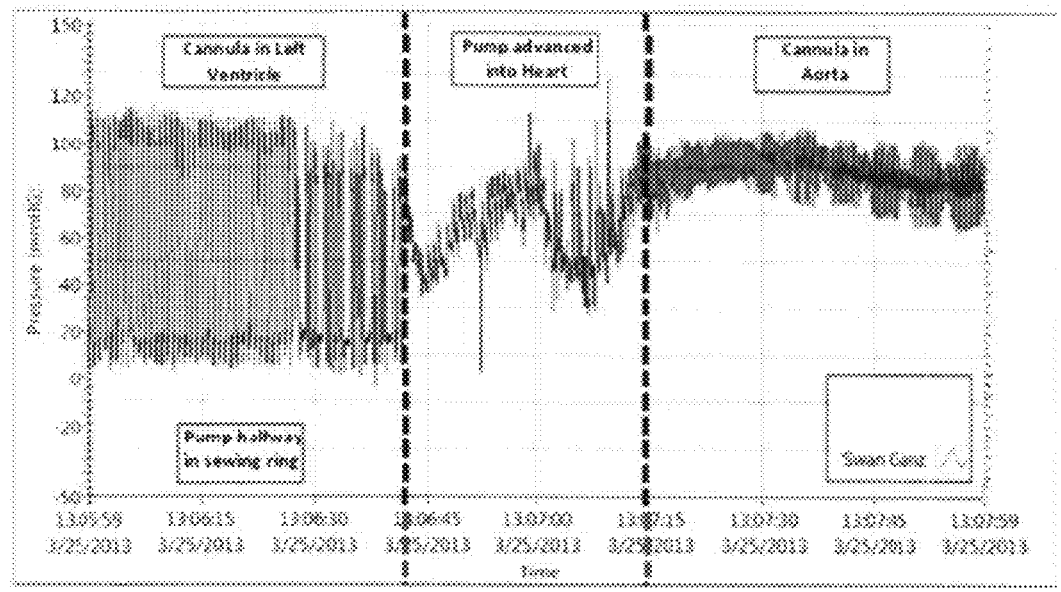
Figure 7:
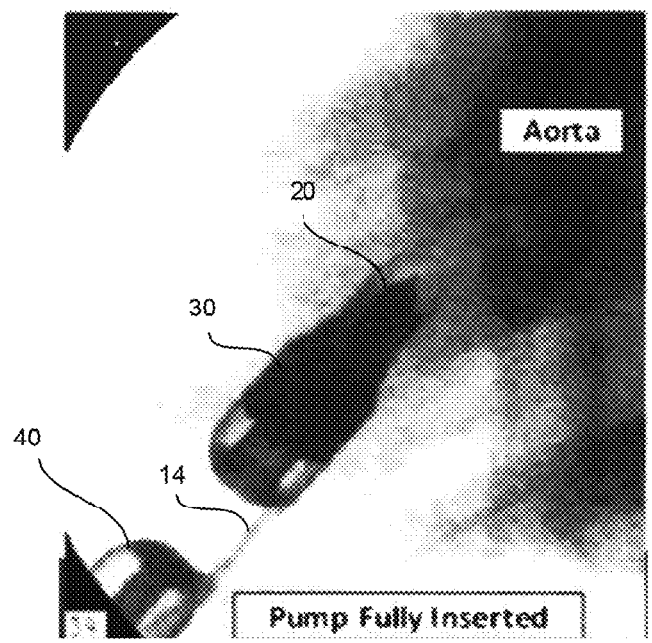

Thus, as illustrated by the pressure wave shown in FIG. 6, as de-aired pump 12, and in particular distal tip 24 of outflow cannula 20, is advanced through the left ventricle, the monitored pressure may indicate when distal tip 24 is located in the ventricle and when it extends through the aortic valve into the aorta. More specifically, a transition of distal tip 24 from the ventricle to the aorta may be indicated by a change in the morphology of the waveform. Another indication can be a change in pressure values, which may be interpreted irrespective of the actual values outputted by the sensor. An even further indication may be a pressure value itself, rather than a change in value, which may be understood by the operator to be a pressure value associated with the aorta and not the ventricle, and vice versa. Also, as illustrated by FIG. 7, the operator may confirm the location of distal tip 24 via fluoroscopy. Thus, catheter 50 helps provide additional confirmation of the location of distal tip 24 relative to the patient's anatomy aside from the usual technique of fluoroscopic imaging.

Once distal tip 24 is properly located within the ascending aorta between the aortic root and aortic arch, pedestal 40 can be attached to the ventricular wall. This may be performed by attaching pedestal 40 to the mounting ring 80 as is known in the art, such as by clamping pedestal 40 with mounting ring 80, for example. At this point, catheter 50 preferably remains within channel 42 of pedestal 40 and, along with resilient seal 44, seals channel 42 during attachment, which helps prevent retrograde blood loss through pedestal 40.

Once pedestal 40 is properly secured, balloon 59 of catheter 50 is deflated or collapsed, which may be performed by withdrawing air or saline solution therefrom. Catheter 50 is pulled proximal to pedestal 40 and catheter body 58 advanced through channel 42 in a distal to proximal direction. Catheter body 58 is withdrawn from inlet port 34 and from channel 42 of pedestal 40. Once catheter body 58 is advanced to a proximal location beyond resilient seal 44, resilient seal 44 closes to provide a one-way temporary seal until channel 42 can be permanently plugged. Channel 42 is permanently plugged by threading or otherwise sealingly engaging the proximal end of channel 42 with closure 46 (best shown in FIG. 8). Pump 12 may then be activated and the access incision closed.

Figure 9:
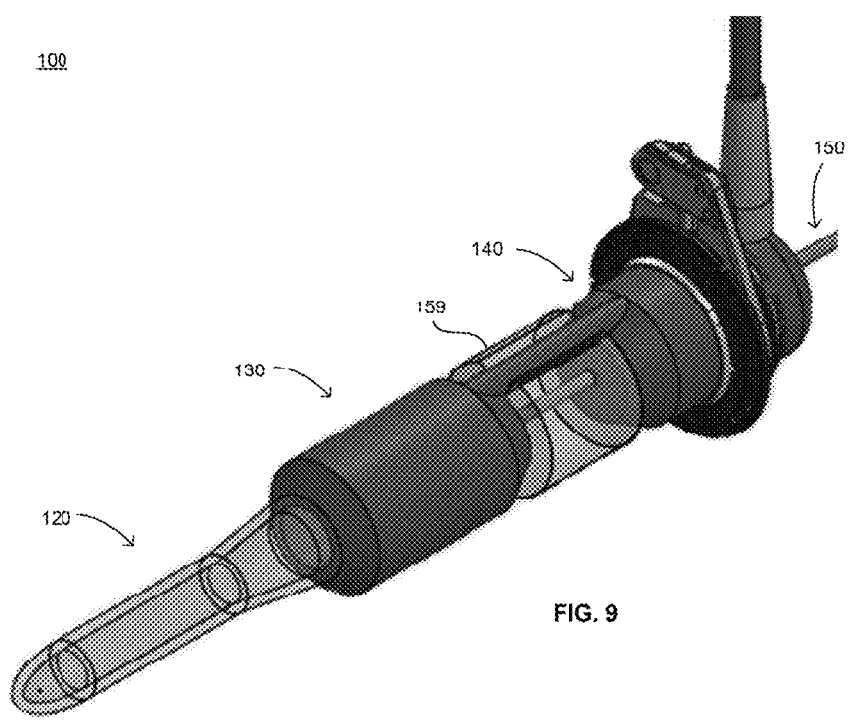
FIG. 9 is a partially transparent perspective view of another embodiment of a transapical VAD implantation kit.

FIG. 9 depicts an alternative transapical VAD implantation kit 100. Kit 100 includes a VAD having a pedestal 140, pump body 130, and outflow cannula 120 similar to that of kit 10, but differs with respect to the catheter 150. Catheter 150 includes an expandable element/balloon 159 that may be cylindrical and dimensioned to tightly/sealingly fit within the space between pedestal 140 and pump body 130 when expanded into an expanded condition. Thus, balloon 159, when expanded, can occlude an inlet of pump body 130 without being disposed therein. In addition, when expanded, balloon 159 may have a diameter as large as that of pedestal 140 and/or pump body 130, and when deflated may have a diameter sufficiently small to slide through a channel within pedestal 140.

Catheter 150 may include balloon 159 in addition to a distal balloon, which may be similar to that of balloon 59 described above and may be configured for placement within the inlet of pump body 130. In such an embodiment, catheter 150 may include a second inflation lumen to feed balloon 159 so that balloon 159 is separately expandable from the distal balloon. Alternatively, balloon 159 may be the only balloon provided with catheter 150.

Balloon 159 helps fill the space between pedestal 140 and pump body 130, which can help reduce blood loss during implantation as it helps prevent blood from flowing around pump body 130 and out of a cored opening in the heart. In other words, as pump body 130 is inserted through a cored opening in the heart, pump body 130 may at least partially occlude the cored opening. However, once pump body 130 is fully inserted into the ventricle but prior to pedestal 140 being placed within the cored opening, blood may flow around pump body 130 into the space between pedestal 140 and pump body 130 and out of the cored opening. Balloon 159 fills this space and helps occlude the cored opening until pedestal 140 is inserted therein.

EXAMPLE

Transapical ventricular assist devices were implanted in healthy bovine (n=4) via a thoracotomy without use of CPB. A Swan-Ganz balloon catheter was inserted into an access channel inside the pedestal and advanced into the pump inflow. A mounting ring was attached at the LV apex and the pump was inserted after coring to form a hole in the wall of the heart. Once the pump was fully inserted through the mounting ring and through the hole in the heart-wall formed by coring, the mounting ring was mechanically engaged with the pedestal so as to hold the pump in place. In this condition, the pedestal and sealing ring closed the hole in the heart wall. The balloon was inflated during pump insertion to prevent retrograde flow through the pump. The fluid lumen of the catheter was used to de-air the pump and was connected to a fluid pressure line and thus to a pressure measuring instrument. Pressure waveforms were monitored during insertion to verify positioning in LV and across the aortic valve. After pump insertion, the balloon was deflated and the catheter was retracted so as to remove the balloon and catheter from the heart through the channel in the pedestal. The proximal end of the channel disposed outside the heart was sealed with a closure in the form of a plug threadedly engaged in the channel.

Results

Average implant time of 5 minutes from LV coring to pump start with less than 50 mL of blood loss was achieved. Swan-Ganz balloon inflation successfully prevented backflow of blood through the pump during insertion. Fluoroscopic images confirmed cannula placement across the aortic valve and pump alignment along the LV outflow tract.

Although the above methods and techniques are described in relation to the implantation of pump 12 into the left ventricle, it should be understood that pump 12 can be implanted into the right ventricle with outflow cannula 20 extending into the pulmonary artery. In addition, it should be understood that catheter 50 can be used in conjunction with other pumps and other delivery approaches without departing from the principles described herein.

Also, while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A pump installation kit, comprising:
a pump including a pump body having an interior and an inlet communicating with the interior, a pumping element mounted within the interior, and an outlet cannula communicating with the interior of the pump body, the pump being adapted for mounting with the pump body and inlet disposed within a ventricle of a heart; and
a temporary plug adapted for releasable, sealing engagement in the inlet.

2. The kit of claim 1, further comprising a securement ring adapted for mounting to the outside of the heart, and a pedestal being adapted for mounting to the securement ring and being mechanically coupled to the pump, the pedestal having a channel having proximal and distal ends, the distal end of the channel communicating with the ventricle and the proximal end of the channel being disposed outside of the heart when the pedestal is mounted to the securement ring.

3. The kit of claim 2, further comprising an elongated element mechanically connected to the temporary plug, the elongated element extending through the channel when the temporary plug is engaged in the inlet, the temporary plug being adapted to pass out of the heart through the channel after the temporary plug is disengaged from the inlet port.

4. The kit of claim 3, wherein the temporary plug has an expanded condition and a collapsed condition, and the temporary plug is adapted to pass out through the channel in the collapsed condition.

5. The kit of claim 3, wherein the elongated element is a catheter having an inflation lumen and the temporary plug includes a balloon communicating with the inflation lumen.

6. The kit of claim 3, wherein the elongated element is a catheter having a fluid lumen, the fluid lumen communicating with the interior of the pump when the temporary plug is engaged in the inlet port.

7. The kit of claim 6, further comprising a pressure measuring instrument connectable to the fluid lumen.

8. The kit of claim 6, further comprising a closure adapted to seal the channel in the pedestal.

9. The kit of claim 8, wherein the closure includes a screw adapted to threadedly engage the channel.

10. The kit of claim 3, further comprising a resilient seal disposed within the channel, the resilient seal sealingly engaging the elongated element and the pedestal when the elongated element is disposed within the channel.

11. The kit of claim 10, wherein the resilient seal is a one-way valve adapted to prevent blood flow from the proximal end of the channel when the elongated element is removed therefrom.

* * * * *